United States Patent
Huang et al.

(10) Patent No.: US 11,814,355 B2
(45) Date of Patent: Nov. 14, 2023

(54) METHOD FOR SYNTHESIZING PITAVASTATIN T-BUTYL ESTER

(71) Applicant: Anhui Qingyun Pharmaceutical and Chemical Co., Ltd., Hefei (CN)

(72) Inventors: Huan Huang, Hefei (CN); Kai Li, Hefei (CN); Qingyun Huang, Hefei (CN); Fuming Zhan, Hefei (CN); Qingguo Huang, Hefei (CN)

( * ) Notice: Subject to any disclaimer, the term of this patent is extended or adjusted under 35 U.S.C. 154(b) by 411 days.

(21) Appl. No.: 17/173,171

(22) Filed: Feb. 10, 2021

(65) Prior Publication Data

US 2022/0041556 A1   Feb. 10, 2022

(30) Foreign Application Priority Data

Aug. 6, 2020 (CN) .......................... 202010783672.X (51) Int. Cl.
| | | |
|---|---|---|
| *C07D 215/14* | (2006.01) | |
| *B01J 31/12* | (2006.01) | |
| *B01J 27/24* | (2006.01) | |
| *B01J 23/30* | (2006.01) | |
| *B01J 27/232* | (2006.01) | |

(52) U.S. Cl.
CPC ............ *C07D 215/14* (2013.01); *B01J 23/30* (2013.01); *B01J 27/232* (2013.01); *B01J 27/24* (2013.01); *B01J 31/121* (2013.01); *B01J 31/122* (2013.01); *B01J 31/128* (2013.01); *B01J 2531/11* (2013.01); *B01J 2531/12* (2013.01)

(58) Field of Classification Search
CPC ......... C07D 215/14; B01J 31/12; B01J 27/24; B01J 23/20
See application file for complete search history.

(56) References Cited

U.S. PATENT DOCUMENTS 8,829,186 B2 *  9/2014  Dwivedi ................. A61P 43/00
546/10

FOREIGN PATENT DOCUMENTS

CN        102174039 A  *  9/2011  ........... C07D 215/12
WO    WO-2007132482 A2 *  11/2007  ........... C07D 215/14

* cited by examiner

*Primary Examiner* — Sikarl A Witherspoon
(74) *Attorney, Agent, or Firm* — Ying-Ting Chen (57) ABSTRACT

A method for synthesizing pitavastatin tert-butyl ester includes obtaining a substance B through reacting (4R-CIS)-6-chloromethyl-2,2-dimethyl-1,3-dioxolane-4-acetic acid tert-butyl ester with a substance A under the action of a first base catalyst, 5 oxidizing with an oxidizing agent to obtain a substance C, then reacting with 2-cyclopropyl-4-(4-fluorophenyl)-quinoline-3-formaldehyde under the action of a second base catalyst to obtain a substance D, and finally, carrying out an acid deprotection to obtain pitavastatin t-butyl ester. The reaction conditions of the present invention are mild and controllable, and the reaction conditions of the synthesis of the Julia olefination do 10 not require an ultra-low temperature reaction. The operation is convenient and simple, the stereoselectivity is good, the yield is high, and the synthesized pitavastatin t-butyl ester is a completely non-cis isomer, and its purity is high.

28 Claims, 4 Drawing Sheets

METHOD FOR SYNTHESIZING PITAVASTATIN T-BUTYL ESTER

CROSS REFERENCE OF RELATED APPLICATION

This application is a non-provisional application that claims the benefit of priority under 35U.S.C. § 119 to a Chinese application number CN111875538A, filed Nov. 3, 2020, which is incorporated herewith by reference in its entirety.

BACKGROUND OF THE PRESENT INVENTION

Field of Invention

The present invention relates to the field of chemical synthesis, and in particular, to a method for synthesizing pitavastatin t-butyl ester.

Description of Related Arts

Pitavastatin calcium is the first fully synthesized HMG-CoA reductase inhibitor jointly developed by the Nissan Chemical and Kowa Company, Ltd.; it is a statin drug. It mainly reduces the ability of the liver to produce cholesterol by inhibiting the liver enzyme of HMG-CoA reductase, thereby improving the blood cholesterol level after elevated. 6-[[(1E)-2-Cyclopropyl-4-(4-fluorophenyl)-3-quinolyl]-vinyl]-2,2-dimethyl-1,3-dioxane-4-acetate tert-butyl ester, which may simply call pitavastatin tert-butyl ester, which is the key intermediate of pitavastatin calcium. In existing pitavastatin calcium synthesis routes, most require the synthesis of this intermediate.

Currently, main synthetic routes of pitavastatin tert-butyl ester are as follows:

One of the synthetic routes is based on the report of Patent Application No. WO2007/132482, a novel process for the preparation of Pravastatin and its pharmaceutically acceptable salts, wherein 3-(bromomethyl)-2-cyclopropyl-4-(4-fluorophenyl) quinoline reacts with triphenylphosphine to produce triphenylphosphonium bromide, which is then reacted with the side-chain aldehyde through Wittig reaction, and is hydrolyzed by hydrochloric acid to obtain pitavastatin t-butyl ester. In the method, since the Wittig reaction will generate a 20% of cis isomer, the yield is not high, and due to the generation of a large amount of triphenylphosphine, the generated three wastes are high, which is not environmental friendly. The synthetic route 1 is as follows:

synthetic route 1

The synthetic route 2 is the preparation method of pitavoctambutyl tert-butyl ester reported in China Patent Number CN102174039A, which utilizes (4R,6S)-6-hydroxymethyl-2,2-dimethyl-1,3-dioxane-4-acetic acid tert-butyl ester as the starting material to react with 1,1'-(1.4-phenylene)-bis-(1H-tetrazole-5-thiol) and di isopropyl azodicarboxylate and subjected to Mitsunobu reaction, then the sulfone compound is obtained through oxidation reaction, and finally the pitavastatin tert-butyl ester is obtained under alkaline conditions with 2-cyclopropyl-4-(4-fluorophenyl) quinoline-3-formaldehyde. The method is relatively harsh in reaction conditions, which requires an ultra-low temperature reaction, and in the oxidation process, because the steric hindrance is high, the selectivity of the conversion is influenced due to a small amount of remaining sulphoxide, which affects the yield and purity of the next reaction. There is a need for multiple column chromatography, and the yield is relatively low. The synthetic route 2 is as follows:

In view of the above, the problem existing in the synthesis method of pitavoctambutyl tert-butyl ester is mainly poor in stereoselectivity, relatively harsh in reaction conditions, incomplete in intermediate oxidation, required for multiple column chromatography, low in yield, and not suitable for industrial production.

SUMMARY OF THE PRESENT INVENTION

With respect to the above problems, the present invention provides a novel synthetic method of pitavastatin tert-butyl ester. The method is mild in reaction condition, good in stereoselectivity, high in yield, high in purity, and easy for industrial production.

The present invention addresses the above-mentioned problems by the following solutions.

The present invention provides a method for synthesizing pitavastatin tert-butyl ester, including the following steps:

obtaining a substance B through reacting (4R-CIS)-6-chloromethyl-2,2-dimethyl-1,3-dioxolane-4-acetic acid tert-butyl ester with a substance A under the action of a first base catalyst; oxidizing with an oxidizing agent to obtain a substance C; then reacting with 2-cyclopropyl-4-(4-fluoro-phenyl)-quinoline-3-formaldehyde under the action of a second base catalyst to obtain a substance D; finally, carrying out an acid deprotection to obtain pitavastatin t-butyl ester. The synthetic route is as follows:

R is selected from the group consisting of hydrogen, alkyl, cycloalkyl, phenyl, and substituted phenyl, and is, preferably, hydrogen or alkyl.

The first base catalyst is selected from the group consisting of sodium carbonate, potassium carbonate, lithium carbonate, cesium carbonate, sodium bicarbonate, potassium bicarbonate, and combinations thereof. Preferably, the first base catalyst is sodium carbonate.

The oxidizing agent is a hydrogen peroxide system or a m-chloroperoxybenzoic acid, and preferably the oxidizing agent is a hydrogen peroxide system. Here, the hydrogen peroxide system is a mixture of hydrogen peroxide and a catalyst, wherein the catalyst is selected from the group consisting of ammonium molybdate tetrahydrate, sodium tungstate, and combination thereof, wherein preferably, the catalyst is ammonium molybdate tetrahydrate.

The second base catalyst is selected from the group consisting of sodium methoxide, sodium ethoxide, lithium tert-butoxide, sodium tert-butoxide, potassium tert-butoxide, sodium hydride, bis-(trimethylsilyl)-amino lithium, bis-(trimethylsilyl)-amino sodium, bis-(trimethylsilyl)-amino sodium potassium, and combinations thereof. Preferably, the second base catalyst is sodium hydride.

The molar ratio of the substance A to the first base catalyst is 1:0.5-5. Preferably, the molar ratio of the substance A to the first base catalyst is 1:1-2.

The molar ratio of (4R-CIS)-6-chloromethyl-2,2-dimethyl-1,3-dioxolane-4-acetic acid tert-butyl ester to substance A is 1:1.1-1.5, preferably 1:1.1-1.3.

The reaction solvent for the synthesized substance B is selected from the group consisting of N, N-dimethylformamide, N, N-dimethylacetamide, toluene, xylene, N-methylpyrrolidone, 1,4-dioxane, and combinations thereof. Preferably, the reaction solvent of the synthesized substance B is 1,4-dioxane.

Further, the weight ratio of the reaction solvent of the synthesized substance B to (4R-Cis)-6-chloromethyl-2,2-dimethyl-1,3-dioxolane-4-acetic acid tert-butyl ester is 1-20:1. Preferably, the weight ratio of the reaction solvent of the synthetic substance B to (4R-Cis)-6-chloromethyl-2,2-dimethyl-1,3-dioxolane-4-acetic acid tert-butyl ester is 5-10:1.

The reaction temperature of the synthesized substance B is 10-100° C. Preferably, the reaction temperature of the synthesized substance B is 30-80° C.

In the oxidation reaction, when the oxidizing agent is a mixture of hydrogen peroxide and a catalyst, the molar ratio of the substance B to the catalyst is 1:0.01-0.5, wherein preferably, the molar ratio of the substance B to the catalyst is 1:0.03-0.1, wherein the molar ratio of the substance B to the hydrogen peroxide is 1:1-20. Preferably, the molar ratio of the substance B to the hydrogen peroxide is 1:4-10.

In the oxidation reaction, when the oxidizing agent is m-chloroperoxybenzoic acid, the molar ratio of the substance B to the m-chloroperoxybenzoic acid is 1:2-10, and preferably, the molar ratio of the substance B to the m-chloroperoxybenzoic acid is 1:2-4.

The temperature of the oxidation reaction is 0-100° C., and preferably, the temperature of the oxidation reaction is 20-40° C.

The oxidation reaction solvent is an alcohol solvent, such as methanol, ethanol, isopropanol, combinations thereof, and etc. Preferably, the oxidation reaction solvent is isopropanol.

The weight ratio of the reaction solvent of the synthesized substance C to the substance B is 1-20:1. Preferably, the weight ratio of the reaction solvent of the synthesized substance C to the substance B is 5-10:1.

The molar ratio of the substance C to the second base catalyst is 1:0.5-10. Preferably, the molar ratio of the substance C to the second base catalyst is 1:1-6.

The molar ratio of the substance C to the 2-cyclopropyl-4-(4-fluorophenyl)-quinoline-3-formaldehyde is 1:1:01-1.3, and preferably is 1:1.01-1.1.

The temperature of the synthesized substance D is −40° C.-20° C. Preferably, the temperature of the synthesized substance D is −10° C.-10° C.

The reaction solvent of the synthesized substance D is selected from the group consisting of tetrahydrofuran, 2-methyltetrahydrofuran, N-methylpyrrolidone, N, N-dimethylformamide, N, N-dimethylacetamide, toluene, dichloromethane, 1.2-dichloroethane, and combinations thereof. Preferably, the solvent of the synthesized substance D is tetrahydrofuran.

When synthesizing the above substance D, the substance C and 2-cyclopropyl-4-(4-fluorophenyl)-quinoline-3-formaldehyde are added to the solvent and stirred and dissolved at room temperature, and then the mixture is cooled to about 0° C., wherein the second base catalyst is slowly added in batches, and the temperature is controlled for continuing the reaction.

Further, the composition D further comprises the steps of concentrating, recrystallizing, and etc.

The solvent in the last step reaction is selected from the group consisting of acetonitrile, toluene, xylene, and combinations thereof. Preferably, the solvent for the hydrolysis is acetonitrile.

The acid in the last step reaction is an acid capable of removing ether protecting groups, such as hydrochloric acid, sulfuric acid, and etc., and the preferable acid is hydrochloric acid. Further preferably, the concentration of the aqueous hydrochloric acid solution is 0.01-1 mol/L in the deprotection process. Preferably, the concentration of the aqueous hydrochloric acid solution is 0.02-0.2 mol/L.

The alkyl group of the present invention refers to a linear or branched alkyl group containing 1 to 6 carbon atoms, including but not limited to methyl, ethyl, n-propyl, isopropyl, n-butyl, isobutyl, n-pentyl, iso-pentyl, n-hexyl, and etc.

According to the present invention, cycloalkyl refers to a saturated monocyclic cyclic hydrocarbon substituent containing from 3 to 6 carbon atoms, including but not limited to cyclopropyl, cyclobutyl, cyclopentyl, cyclohexyl, and etc.

The substituted phenyl described in the present invention refers to one, two or more substitutions at any location(s) on the benzene ring. The substituent is selected from the group consisting of hydrogen, halogen, nitro, cyano, C, 1-C4 alkyl.

The C, 1-C4 alkyl refers to a linear chain or branched chain alkyl group containing 1 to 4 carbon atoms, including but not limited to methyl, ethyl, n-propyl, isopropyl, n-butyl, isobutyl, and etc.

Those reagents without specified source in the present invention are regular or conventional reagents available on the market.

In contrasting with the prior art, the present invention has the following beneficial effects:

(1) The present invention utilizes Julia olefination, which does not require an ultra-low temperature reaction, and the constructed double bond is almost free of cis isomer production, which is good in stereoselectivity and high in purity; and the pitavastatin t-butyl ester obtained after the last step reaction of acid hydrolysis has no cis isomer at all;

(2) Due to the adoption of thiazole ring in the reaction of synthesizing substance B, oxidation is easy to occur and the conversion is complete that the yield of the first two-step reaction can reach more than 81.6%; in addition, in the reaction of synthesizing substance D, the space steric hindrance of thiazole ring is small, and it is easy to leave, so that the product purity is good and the yield is high;

(3) In contrasting with traditional dimensional hash reaction, thanks to the characteristic that the substance D generates almost no cis isomer, the conversion rate is increased, the difficulty of separating the isomer and the three-waste problem caused by post-treatment are reduced;

(4) In the method for synthesizing pitavastatin t-butyl ester, the reaction conditions of each of the steps are mild and controllable, the operation is convenient and simple, and the method is suitable for industrial production.

DETAILED DESCRIPTION OF THE PREFERRED EMBODIMENT

Figure 1:
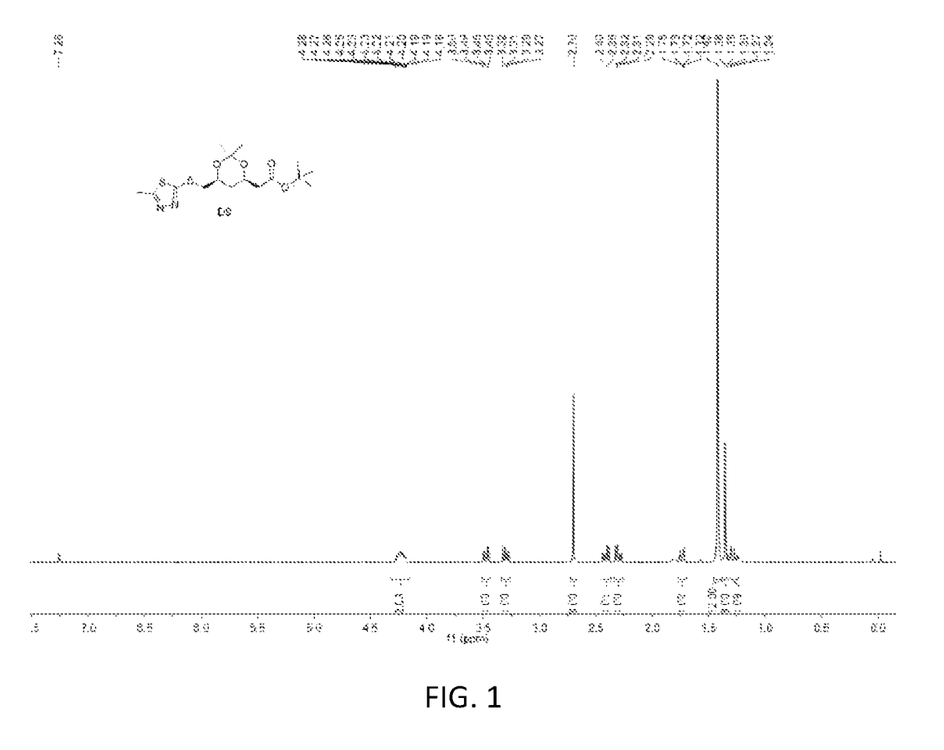
FIG. 1 is a nuclear magnetic hydrogen spectrum diagram of the substance B according to a preferred embodiment 1 of the present invention.
Figure 2:
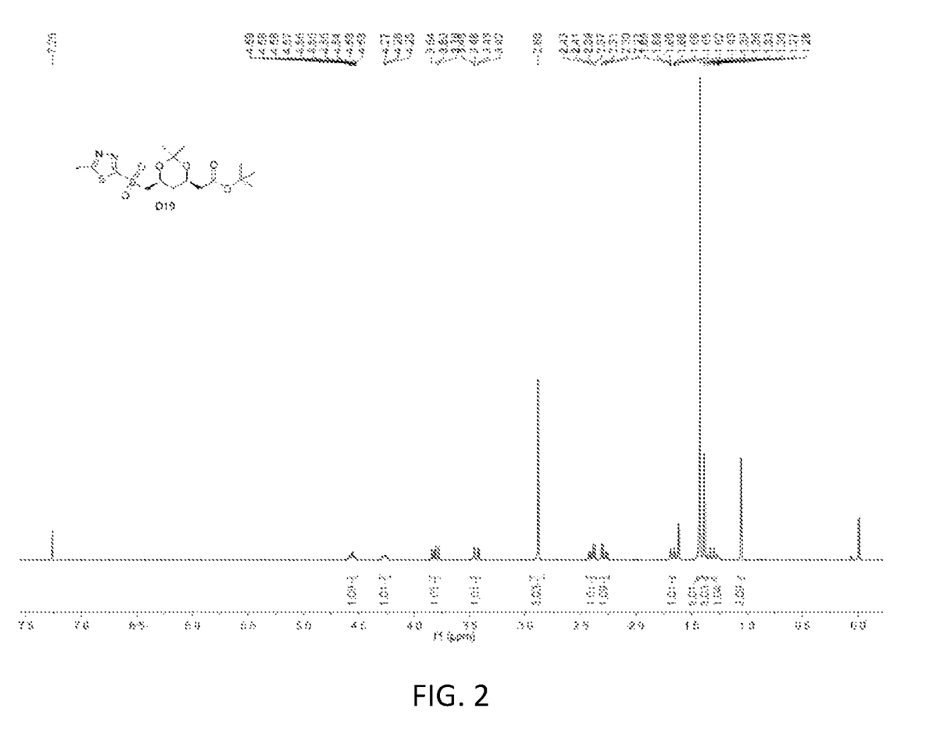
FIG. 2 is a nuclear magnetic hydrogen spectrum diagram of the substance C according to the above preferred embodiment 1 of the present invention.
Figure 3:
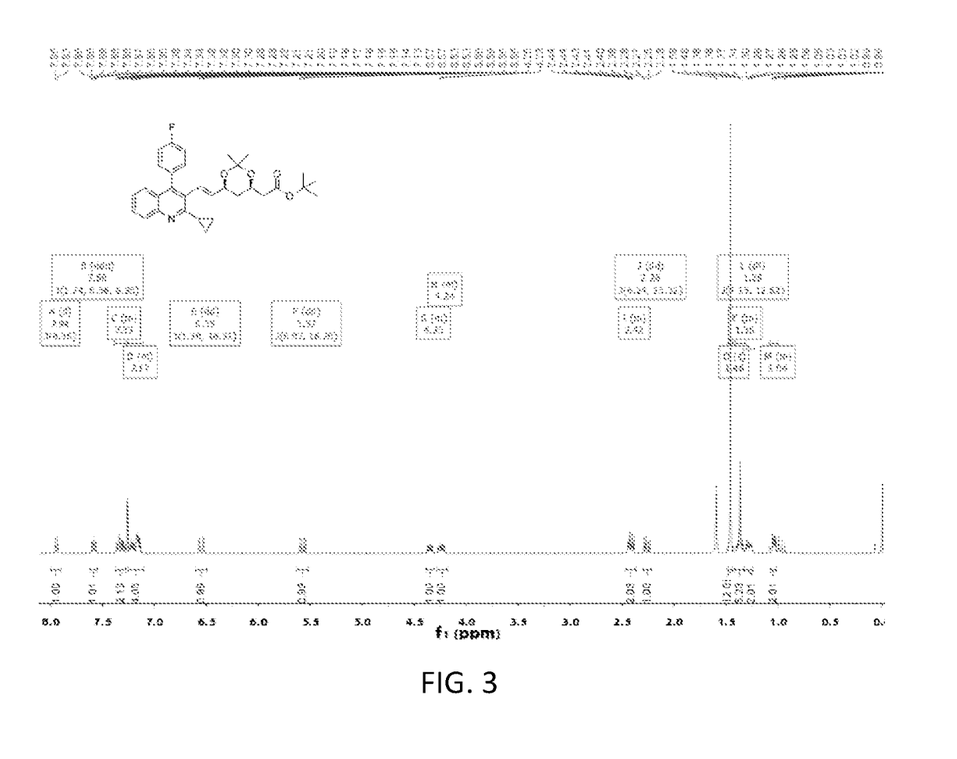
FIG. 3 is a nuclear magnetic hydrogen spectrum diagram of the substance D according to the above preferred embodiment 1 of the present invention.
Figure 4:
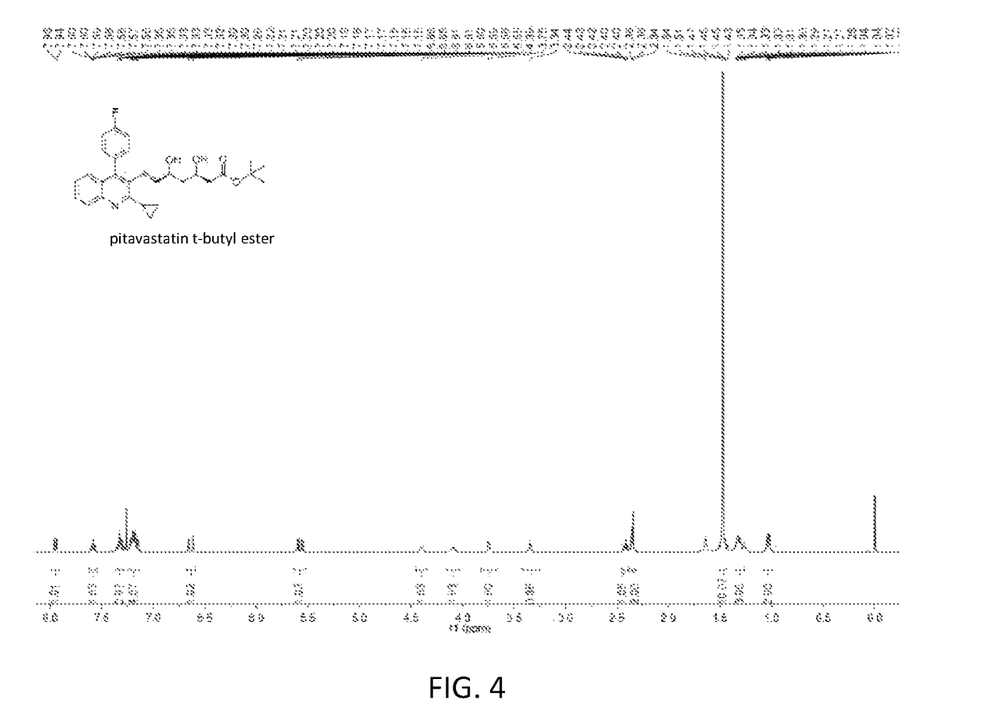
FIG. 4 is a nuclear magnetic hydrogen spectrum diagram of the pitavastatin tert-butyl ester.

Technical solutions of the present invention will be described in detail through preferred specific embodiments as follows.

Embodiment 1 (R is Methyl)

Under nitrogen protection, sequentially add sodium carbonate 160 g (1.5 mol, 3.0 eq), (4R-Cis)-6-chloromethyl-2,2-dimethyl-1,3-dioxolane-4-acetic acid tert-butyl ester 139.5 g (0.5 mol, 1.0 eq), 1,4-dioxane 700 g, 2-mercapto-5-methyl-1,3,4-thiadiazole 79 g (0.6 mol, 1.2 eq) into a 2000 ml four-port round bottom flask, stirring, slowly raising the temperature to 80° C., stirring and reacting for 6 h, and sampling for TLC (the expanding agent is petroleum ether:ethyl acetate=1:1 v/v). After the raw materials have been tested and confirmed completely converted, perform reduced pressure concentration to remove the solvent 1,4-dioxane, adding 500 ml of water, 500 ml of ethyl acetate, continuing stirring for 15 minutes, standing for layering, and separating the organic phase, wherein the aqueous phase is extracted with ethyl acetate 500 ml X 2, and the organic phases are combined. The brownish black oily substance B is obtained after the concentration.

195 g (with a small amount of solvent), purity 93.7%. It is directly used for the next oxidation reaction without purification.

Sequentially add the substance B oil (theoretical weight 187 g, 0.5 mol), isopropanol alcohol 800 g, and ammonium molybdate tetrahydrate 30.9 g (0.025 mol, 0.05 eq) into a 2000 ml four-port round bottom flask, slowly adding dropwise 30% hydrogen peroxide 339 g (i.e., hydrogen peroxide of 3.0 mol) in 3 h at room temperature. Then, raise the temperature to 50° C., and keeping the temperature for 24 h, wherein it will then precipitate a large amount of white solid, sampling and TLC (the expanding agent is petroleum ether: ethyl acetate=1:2 v/v) detecting complete conversion of the raw materials, cooling to 0° C., filtering, washing the filter cake with 200 ml of water to obtain a white substance C wet product, fan drying at 55° C. for 24 h to obtain 177 g of substance C, 99.7% of purity, and 87.2% of the total yield of the two steps.

Add the substance C 177 g (0.44 mol), 2-cyclopropyl-4-(4-fluorophenyl)-quinoline-3-formaldehyde 133 g (0.45 mol, 1.05 eq), and tetrahydrofuran 420 g into a 1000 ml four-necked round bottom flask, starting stirring, cooling to 0° C., adding 34.8 g (0.87 mol) of sodium hydride (60%) in batches, controlling the temperature to not exceed 10° C., stirring for 2 h at 10° C. after the addition, slowly raising the temperature to 25° C., continuing to react for 2 h, and sampling for TLC detection (the spreading agent is petroleum ether:ethyl acetate=2:1 v/v) adding 200 mL of saturated sodium bicarbonate aqueous solution into the reaction system for quenching, concentrating to remove tetrahydrofuran to obtain a substance D crude product, dissolving by 800 mL toluene, extracting the toluene phase, drying, concentrating to obtain a solid, then recrystallizing the solid by 1200 mL methanol to obtain the substance D pure product 199 g, purity: 99.8%, and yield: 88.3%.

Add the substance D 150 g (0.29 mol) and acetonitrile 680 g into a 2000 ml four-neck round bottom flask, slowly heating to around 40° C. and stirring to dissolve clearly, slowly dropwise adding 300 ml of hydrochloric acid with a concentration of 0.02 mol/L, carrying out heat preservation reaction for 2 h after the dropwise addition, performing HPLC detection to confirm complete conversion of the raw material, cooling to 0° C., dropwise adding a saturated sodium carbonate aqueous solution to adjust the pH of the reaction system to about 7, continuing to stir for 3 h, filtering, washing, and drying to obtain the white pitavastatin tert-butyl ester pure product 131G, wherein the purity is 99.9%, and the yield is 94.7%.

H1 NMR (400 MHz, CDCl$_3$): δ 1.03 (dd, J1=2.13 Hz, J2=8.10 Hz, 2H), 1.26-1.35 (m, 3H), 1.13-1.64 (m, 10H), 2.34-2.36 (m, 2H), 2.40-2.44 (ddd, J1=4.02 Hz, J2=6.47 Hz, J3=8.12 Hz, 1H), 3.34 (s, 1H), 3.75 (s, 1H), 4.15-4.11 (m, 1H), 4.36-4.41 (m, 1H), 5.55-5.59 (dd, J1=6.11 Hz, J2=16.15 Hz, 1H), 6.60-6.66 (dd, J1=1.26 Hz, J2=16.15 Hz, 11-1), 7.15-7.20 (m, 4H), 7.21-7.26 (m, 211), 7.57-7.60 (ddd, J1=1.83 Hz, J2=6.42 Hz, J3=8.36 Hz, 1H), 7.95 (d, J=8.33 Hz, 1H).

Embodiment 2 (R is Benzyl)

Under nitrogen protection, sequentially add carbonic potassium 207 g (1.5 mol, 3.0 eq), (4R-Cis)-6-chloromethyl-2,2-dimethyl-1,3-dioxolane-4-acetic acid tert-butyl ester 139.5 g (0.5 mol, 1.0 eq), N, N-dimethylformamide 700 g, 2-mercapto-5-benzyl-1,3,4-thiadiazole 116 g (0.6 mol, 1.2 eq) into a 2000 ml four-port round bottom flask, stirring, slowly raising the temperature to 80° C., stirring and reacting for 6 h, and sampling for TLC (the expanding agent is petroleum ether:ethyl acetate=1:1 v/v). After the raw materials have been tested and confirmed completely converted, perform reduced pressure concentration to remove the solvent N, N-dimethylformamide, adding 500 ml of water, 500 ml of ethyl acetate, continuing stirring for 15 minutes, standing for layering, and separating the organic phase, wherein the aqueous phase is extracted with ethyl acetate 500 ml X 2, and the organic phases are combined. The brownish black oil substance B 225 g (with a small amount of solvent) was concentrated and obtained, wherein the purity is 94.7%. It is directly used for the next oxidation reaction without purification.

Sequentially add the substance B oil (theoretical weight 218 g, 0.5 mol), methanol 800 g, sodium tungstate 16.5 g (0.05 mol) into a 2000 ml four-port round bottom flask at room temperature, slowly dropwise adding 30% hydrogen peroxide 339 g (i.e., hydrogen peroxide of 3.0 mol) in 3 h, then raising the temperature to 50° C., keeping the temperature for 24 h, wherein it will precipitate a large amount of white solid, sampling and TLC (the expanding agent is petroleum ether:ethyl acetate=1:2 v/v) for detecting complete conversion of the raw materials, cooling to 0° C., filtering, washing the filter cake with 200 ml of water to obtain a white substance C wet product, fan drying at 55° C. for 24 h to obtain 209 g of substance C, 99.7% of purity, and 89.2% of the total yield of the two steps.

Add the substance C 205 g (0.44 mol), 2-cyclopropyl-4-(4-fluorophenyl)-quinoline-3-formaldehyde 133 g (0.45 mol, 1.05 eq), and tetrahydrofuran 690 ml into a 1000 ml four-necked round bottom flask and staring stirred, cooled to −10° C., and adding sodium tert-butoxide 83.6 g (0.87 mol) in batches, wherein the temperature is controlled not exceed 0° C., after addition, the mixture is stirred for 2 h at 0° C., then slowly heated to 25° C. for the reaction to be continued for 2 h, wherein TLC detection is carried out (the expanding agent is petroleum ether:ethyl acetate=2:1 v/v) to confirm that the raw material conversion is complete, adding a 200 mL saturated sodium bicarbonate aqueous solution into the reaction system for quenching, concentrating tetrahydrofuran to obtain a substance D crude product, dissolving the crude product D crude product with 800 mL of toluene, so that the toluene phase is extracted, drying and concentrating to obtain a solid, so the solid is then recrystallized from 1200 mL of methanol to obtain the substance D pure product 203 g, wherein the purity is 99.8% and the yield is 89.6%.

Add the substance D 150 g (0.29 mol) and acetonitrile 700 g into a 2000 ml four-neck round bottom flask, slowly heating to around 40° C. and stirring to dissolve clearly, slowly dropwise adding 150 ml of hydrochloric acid with a concentration of 0.04 mol/L, carrying out heat preservation reaction for 2 h after the dropwise addition, performing HPLC detection to confirm complete conversion of the raw material, cooling to 0° C., dropwise adding a saturated sodium carbonate aqueous solution to adjust the pH of the reaction system to about 7, continuing to stir for 3 h, filtering, washing, and drying to obtain the white pitavastatin tert-butyl ester pure product 129G, wherein the purity is 99.7%, and the yield is 93.2%.

Embodiment 3

The substituent of the substance A is cyclopropyl, whereas the rest of the conditions and feeding ratios are consistent to Embodiment 1.

Embodiment 4

The substituent of the substance A is hydrogen base, whereas the rest of the conditions and feeding ratios are consistent to Embodiment 1.

Embodiment 5

The first base catalyst is sodium bicarbonate, and the molar ratio of the substance A to the sodium bicarbonate is 1:0.5. The second base catalyst is sodium methoxide, and the molar ratio of the substance C to the sodium methoxide is 1:0.5. The ammonium molybdate tetrahydrate is replaced with sodium tungstate in the oxidation reaction; the rest is consistent with Embodiment 1.

Embodiment 6

The first base catalyst is potassium bicarbonate, and the molar ratio of the substance A to the potassium bicarbonate is 1:5. The second base catalyst is bis-(trimethylsilyl)-amino lithium, and the molar ratio of the substance C to the bis-(trimethylsilyl)-amino lithium is 1:10. The rest is consistent with Embodiment 1.

Embodiment 7

The temperature of the synthesized substance B is 10° C. and the time is 8 hours. In the synthesis process of the substance C, the oxidation temperature is 0° C., and the oxidation time is 48 hours. The rest is consistent with Embodiment 1.

Embodiment 8

The temperature of the synthesized substance B is 100° C. and the time is 2 hours. In the synthesis process of the substance C, the oxidation temperature is 100° C., and the oxidation time is 12 hours. The rest is consistent with Embodiment 1.

The purity and yield of the contents of the products of each of the steps, the contents of the isomers of the product D and pitavastatin tert-butyl ester in Embodiments 1-8 were detected and calculated as follows:

| Name | Item | Embodiment 1 | Embodiment 2 | Embodiment 3 | Embodiment 4 |
| --- | --- | --- | --- | --- | --- |
| substance C | yield (%) | 87.2 | 89.2 | 85.4 | 92.1 |
|  | purity (%) | 99.7 | 99.7 | 99.8 | 99.8 |
| substance D | yield (%) | 88.3 | 89.6 | 82.5 | 89.3 |
|  | purity (%) | 99.8 | 99.8 | 99.7 | 99.8 |
|  | content of cis-isomer | 0.06 | 0.07 | not detected | not detected |
| pitavastatin t-butyl ester | yield (%) | 94.7 | 93.2 | 95.2 | 95.1 |
|  | purity (%) | 99.9 | 99.7 | 99.7 | 99.9 |
|  | content of cis-isomer | not detected | not detected | not detected | not detected |

-continued

| Name | Item | Embodiment 5 | Embodiment 6 | Embodiment 7 | Embodiment 8 |
|---|---|---|---|---|---|
| substance C | yield (%) | 96.4 | 81.6 | 83.2 | 84.7 |
| | purity (%) | 99.8 | 99.5 | 99.4 | 99.7 |
| substance D | yield (%) | 81.2 | 83.2 | 84.1 | 83.8 |
| | purity (%) | 99.9 | 99.8 | 99.6 | 99.3 |
| | content of cis-isomer | 0.02 | not detected | 0.05 | 0.06 |
| pitavastatin t-butyl ester | yield (%) | 94.1 | 91.9 | 92.7 | 93.5 |
| | purity (%) | 99.8 | 99.9 | 99.5 | 99.8 |
| | content of cis-isomer | not detected | not detected | not detected | not detected |

As it can be seen from the above embodiments and the above table, the reaction conditions of the present invention are mild, the stereoselectivity is good, and there is no cis-isomer in the obtained pitavastatin tert-butyl ester, which purity and yield are high.

The foregoing is a description of preferred specific embodiments of the present invention. It is to be understood that the present invention is not limited to the above-described embodiments, which are only intended to illustrate the principles of the present invention. Various non-substantial variations and modifications may be made by those skilled in the art without departing from the spirit and construct of the present invention, all of which fall within the scope of the claimed invention.

What is claimed is:

1. A method for synthesizing pitavastatin t-butyl ester, comprising the steps of:
    (a) obtaining a substance B through reacting (4R-CIS)-6-chloromethyl-2,2-dimethyl-1,3-dioxolane-4-acetic acid tert-butyl ester with a substance A under an action of a first base catalyst;
    (b) oxidizing with an oxidizing agent to obtain a substance C;
    (c) reacting with 2-cyclopropyl-4-(4-fluorophenyl)-quinoline-3-formaldehyde under an action of a second base catalyst to obtain a substance D; and
    (d) carrying out an acid deprotection to obtain pitavastatin t-butyl ester, wherein a structural formula of said substance A, said substance B, said substance C, said substance D, and said pitavastatin t-butyl ester is as follows:

substance A substance B substance C substance D pitavastatin t-butyl ester

R is one of hydrogen, alkyl, cycloalkyl, phenyl, and substituted phenyl.

2. The method, as recited in claim 1, wherein the R is one of hydrogen and alkyl.

3. The method, as recited in claim 1, wherein said first base catalyst is selected from the group consisting of sodium carbonate, potassium carbonate, lithium carbonate, cesium carbonate, sodium bicarbonate, potassium bicarbonate, and combinations thereof.

4. The method, as recited in claim 2, wherein said first base catalyst is sodium carbonate.

5. The method, as recited in claim 1, wherein said oxidizing agent is one of a system and m-chloroperoxybenzoic acid, wherein the hydrogen peroxide system is a mixture of hydrogen peroxide and a catalyst, wherein said catalyst is selected from the group consisting of ammonium molybdate tetrahydrate, sodium tungstate, and combination thereof.

6. The method, as recited in claim 3, wherein said oxidizing agent is one of a system and m-chloroperoxybenzoic acid, wherein the hydrogen peroxide system is a mixture of hydrogen peroxide and a catalyst, wherein said catalyst is selected from the group consisting of ammonium molybdate tetrahydrate, sodium tungstate, and combination thereof.

7. The method, as recited in claim 4, wherein said oxidizing agent is a hydrogen peroxide system, wherein the hydrogen peroxide system is a mixture of hydrogen peroxide and a catalyst, wherein said catalyst is ammonium molybdate tetrahydrate.

8. The method, as recited in claim 1, wherein the second base catalyst is selected from the group consisting of sodium methoxide, sodium ethoxide, lithium tert-butoxide, sodium tert-butoxide, potassium tert-butoxide, sodium hydride, bis-(trimethylsilyl)-amino lithium, bis-(trimethylsilyl)-amino sodium, bis-(trimethylsilyl)-amino sodium potassium, and combinations thereof.

9. The method, as recited in claim 6, wherein the second base catalyst is selected from the group consisting of sodium methoxide, sodium ethoxide, lithium tert-butoxide, sodium tert-butoxide, potassium tert-butoxide, sodium hydride, bis-(trimethylsilyl)-amino lithium, bis-(trimethylsilyl)-amino sodium, bis-(trimethylsilyl)-amino sodium potassium, and combinations thereof.

10. The method, as recited in claim 7, wherein said second base catalyst is sodium hydride.

11. The method, as recited in claim 1, wherein said reaction solvent for said synthesized substance B is selected from the group consisting of N, N-dimethylformamide, N, N-dimethylacetamide, toluene, xylene, N-methylpyrrolidone, 1,4-dioxane, and combinations thereof.

12. The method, as recited in claim 8, wherein said reaction solvent for said synthesized substance B is selected from the group consisting of N, N-dimethylformamide, N, N-dimethylacetamide, toluene, xylene, N-methylpyrrolidone, 1,4-dioxane, and combinations thereof.

13. The method, as recited in claim 10, wherein said reaction solvent for said synthesized substance B is 1,4-dioxane.

14. The method, as recited in claim 1, wherein said oxidation reaction solvent is selected from the group consisting of methanol, ethanol, isopropanol, and combinations thereof.

15. The method, as recited in claim 12, wherein said oxidation reaction solvent is selected from the group consisting of methanol, ethanol, isopropanol, and combinations thereof.

16. The method, as recited in claim 13, wherein said oxidation reaction solvent is isopropanol.

17. The method, as recited claim 1, wherein the molar ratio of said substance A to said first base catalyst is 1:0.5-5.

18. The method, as recited claim 15, wherein the molar ratio of said substance A to said first base catalyst is 1:0.5-5.

19. The method, as recited in claim 16, wherein the molar ratio of said substance A to said first base catalyst is 1:1-2.

20. The method, as recited in claim 1, wherein the molar ratio of said substance B to said catalyst is 1:0.01-0.5, and the molar ratio of said substance B to said hydrogen peroxide is 1:1-20.

21. The method, as recited in claim 18, wherein the molar ratio of said substance B to said catalyst is 1:0.01-0.5, and the molar ratio of said substance B to said hydrogen peroxide is 1:1-20.

22. The method, as recited in claim 19, wherein the molar ratio of said substance B to said catalyst is 1:0.03-0.1, and the molar ratio of said substance B to said hydrogen peroxide is 1:4-10.

23. The method, as recited in claim 1, wherein the molar ratio of said substance C to said second base catalyst is 1:0.5-10.

24. The method, as recited in claim 21, wherein the molar ratio of said substance C to said second base catalyst is 1:0.5-10.

25. The method, as recited in claim 22, wherein the molar ratio of said substance C to said second base catalyst is 1:1-6.

26. The method, as recited in claim 1, wherein the reaction temperature of said synthetic substance B is 10-100° C., the temperature of said oxidation reaction is 0-100° C., and the temperature of said synthesized substance D is 40-30° C.

27. The method, as recited in claim 24, wherein the reaction temperature of said synthetic substance B is 10-100° C., the temperature of said oxidation reaction is 0-100° C., and the temperature of said synthesized substance D is 40-30° C.

28. The method, as recited in claim 25, wherein the reaction temperature of said synthesize substance B is 30-80° C., the temperature of said oxidation reaction is 20-50° C. and the temperature of said synthesized substance D is −10-10° C.

* * * * *